US006720143B2

(12) United States Patent
Juncosa et al.

(10) Patent No.: US 6,720,143 B2
(45) Date of Patent: Apr. 13, 2004

(54) GENETIC ASSAY SYSTEM

(75) Inventors: Robert D. Juncosa, Yardley, PA (US); Rene Bongard, Princeton, NJ (US); Johannes Dapprich, Lawrenceville, NJ (US); Richard Scribner, Shingle Springs, CA (US)

(73) Assignee: Orchid BioSciences, Inc., Princeton, NJ (US)

(*) Notice: Subject to any disclaimer, the term of this patent is extended or adjusted under 35 U.S.C. 154(b) by 2 days.

(21) Appl. No.: 09/844,980

(22) Filed: Apr. 27, 2001

(65) Prior Publication Data

US 2001/0051113 A1 Dec. 13, 2001

Related U.S. Application Data

(63) Continuation of application No. 09/321,170, filed on May 27, 1999, now Pat. No. 6,225,109.

(51) Int. Cl.[7] ............................ C12Q 1/68; C12M 1/00; C12M 1/36; G01N 15/06

(52) U.S. Cl. ..................... 435/6; 435/283.1; 435/287.2; 435/288.3; 435/288.5; 422/50; 422/58; 422/68.1

(58) Field of Search ........................... 435/288.5, 288.3, 435/287.2, 6; 422/50, 58, 68.1

(56) References Cited

U.S. PATENT DOCUMENTS

| | | | | |
|---|---|---|---|---|
| 5,517,870 A | * | 5/1996 | Kurimura et al. | 73/865.5 |
| 5,928,880 A | * | 7/1999 | Wilding et al. | 435/7.21 |
| 5,958,760 A | | 9/1999 | Freeman | |
| 6,176,962 B1 | * | 1/2001 | Soane et al. | |
| 6,198,869 B1 | * | 3/2001 | Kraus et al. | 385/129 |
| 6,225,109 B1 | * | 5/2001 | Juncosa et al. | |
| 6,322,683 B1 | * | 11/2001 | Wolk et al. | |

FOREIGN PATENT DOCUMENTS

| | | | |
|---|---|---|---|
| EP | WO 98/22799 | * | 5/1998 |

* cited by examiner

*Primary Examiner*—B J Forman
(74) *Attorney, Agent, or Firm*—Kevin G. Mierzwa

(57) ABSTRACT

A genetic analysis device particularly for determining the presence or absence of Single Nucleotide Polymorphisms (SNPs) within specific sequences of DNA. The device includes a housing, at least one glass slide member, and an elastomeric member with channels thereon. Oligo arrays are spotted on the glass slide member(s) and subjected to DNA samples, reagents or the like. A plurality of openings or ports allow entry of samples, reagents or wash materials, while a plurality of exit ports or openings allow removal of such materials. The assay devices can be used for multiple samples or a single sample. A plurality of synthesis devices can be positioned in a support base in order to allow sampling in an automated manner. The synthesis devices can be provided in a 96 well microtiter format.

14 Claims, 11 Drawing Sheets

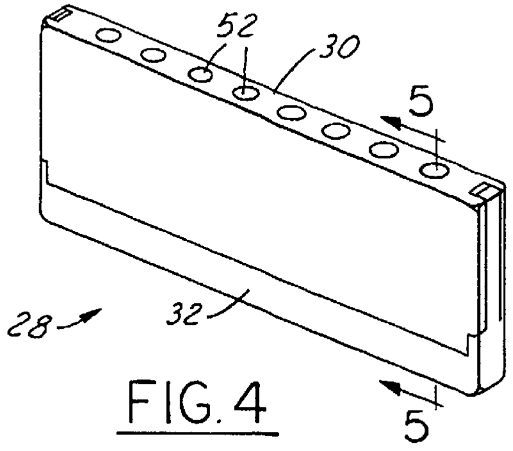
FIG. 4
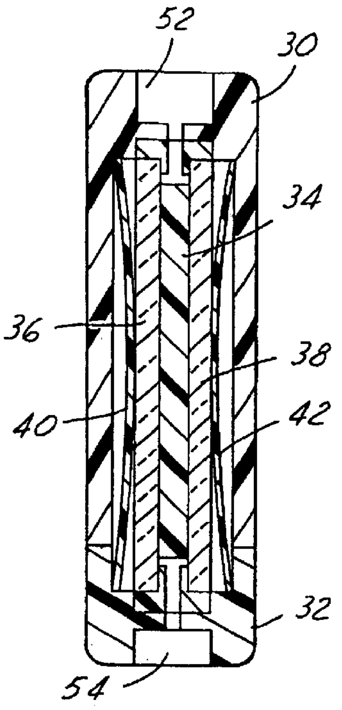
FIG. 5
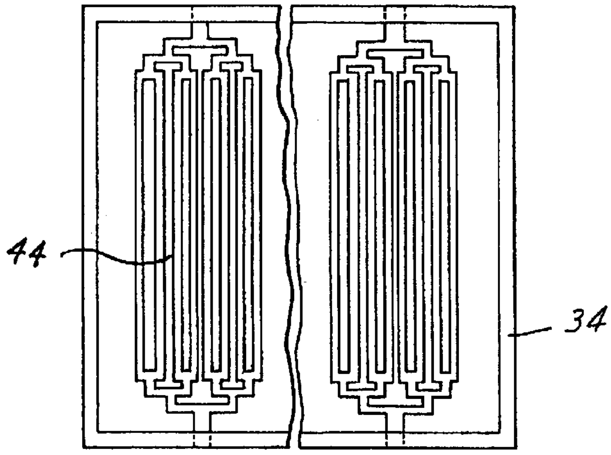
FIG. 7
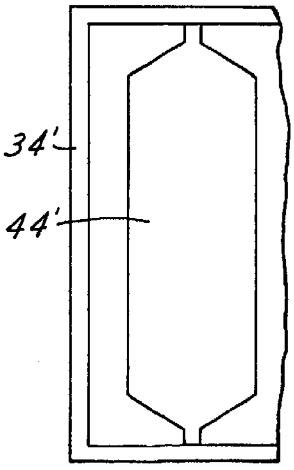
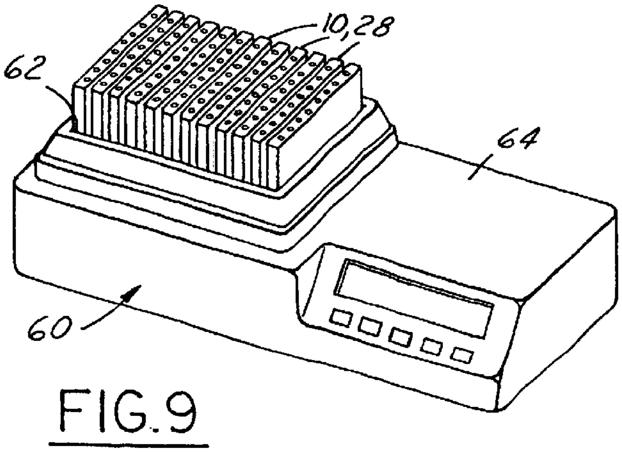
FIG. 9
FIG. 8

GENETIC ASSAY SYSTEM

CROSS-REFERENCE TO RELATED APPLICATIONS

This application is a continuation of U.S. patent application Ser. No. 09/321,170, filed May 27, 1999 now U.S. Pat. No. 6,225,109. This application is related to the subject matter of U.S. patent application Ser. No. 09/321,410, entitled "Multiple Fluid Sample Processor and System. The disclosure of which is hereby incorporated by reference herein.

TECHNICAL FIELD

The present invention relates to devices, systems and methods for genetic diagnostic applications, particularly to determine the presence or absence of Single Nucleotide Polymorphisms (SNP) within specific sequences of DNA.

BACKGROUND OF THE INVENTION

The detection and screening of Single Nucleotide Polymorphisms (SNPs), is receiving increasing interest and effort in genomics research. SNPs are the most common type of DNA sequence variation and efforts are being made to generate sufficiently dense genetic maps for complex trait mapping. As a result, the number of SNP samples tested per year is increasing at a significant rate.

It is believed that SNPs are indicators to determine the pre-disposition of patients to diseases such as cancer, cardiovascular disease and other pathologies. SNPs also have application in pharmacogenetic applications and drug development, such as drug toxicity, metabolism, and efficacy. Further, SNPs have application for identifying bacterial mechanisms of antibiotic resistance. Scanning the human genome for sequence variations could identify millions of potentially informative genetic markers. These diagnostic applications require a large number of SNPs for definitive indications and should be compared against a large number of samples for accuracy.

Some of the sampling effort has been focused on oligo arrays, as well as other genetically based diagnostic applications. However, the present state of instrumentation, informatics and associated cost restrict the number of samples that can be run against these arrays.

It is an object of the present invention to provide devices, methods and systems for detection and screening of SNPs, particularly for detecting and screening SNPs on a faster and volumetric basis. It is also an object of the present invention to provide such apparatuses, methods and systems which are relatively inexpensive, easy-to-use and have flexibility or versatility in their uses.

It is a further object of the present invention to provide devices, systems and methods for detecting and screening of SNPs that make minimal use of custom automation and instrumentation. In this regard, it is desirable to utilize conventional instrumentation, such as fluid handling equipment and fluorescence readers.

It is still a further object of the present invention to provide devices, methods and systems for detecting and screening of SNPs that can screen large numbers of samples and at the same time minimize the required material volumes and resultant costs. It is an additional object of the present invention to provide a fluid sampling device with separate components and which can be disassembled, and which does not utilize separate gasket members or adhesives to hold and seal the components together.

SUMMARY OF THE INVENTION

In accordance with the present invention, devices, methods and systems are provided which perform genetic assays, particularly to determine the presence or absence of Single Nucleotide Polymorphisms (SNPs) within specific sequences of DNA. The inventive system basically comprises two main components, an analysis or assay device and a support base. The analysis device contains a housing, a multi-port middle application layer, and at least one glass slide member for specimens. The middle layer is made of a compliant, moldable, elastomer material with a plurality of channels or cavities molded into it. For example, the middle layer can be made from a polydimethylsiloxane (PDMS) material or a liquid silicone rubber (LSR) material, although the invention is not limited to these two materials. Each slide member contains spots or sites that comprise arrays of deposited oligonucleotides, each designed to detect a SNP of interest. The number of SNP tests per device depends on the design of the channels or cavities and the density of the array. The middle layer creates a tight liquid seal against the glass slide when the device is assembled. PDMS and LSR, in particular, have an affinity to stick tightly to glass and provide a reversible liquid tight seal. With the present invention, micro-sized channels and cavities can be formed within the self-sealing middle layer. Separate sealing members or adhesives are not needed to hold and seal the component members together.

Openings or ports are provided at opposite ends or surfaces of the analysis device, the ports being in liquid communication with the channels or cavities in the middle layer. The channels or cavities can be designed to address specific product requirements and preferably are very small microsized members. Also, due to the self-sealing characteristics of the middle layer, additional sealing devices or mechanisms are unnecessary at the ports and channels.

The middle layer and slide member(s) are positioned inside the housing. Two portions of the housing or frame member are snapped or otherwise held together forming the housing and holding the assembly together. Biasing members could also be provided if necessary to apply a constant slight pressure to the slide and middle member, if necessary, in order to improve the seal between them.

In use, appropriate liquid materials are introduced sequentially into the ports at one end or side of the analysis device in order to perform the assay or analysis intending to identify and/or detect the presence or absence of SNPs. Waste materials exit from ports in the opposite side of the device. Wash materials and reagents are circulated through the device as required.

Other embodiments of assay devices can also be utilized. A single sample device includes a cover-type housing in which a compliant, elastomer material and glass slide are positioned, the housing having only a single port for entry of DNA, reagents and other materials to form the SNPs from oligos spotted on the slide. An absorbent material can collect the waste materials which flow past the spots.

A plurality of assay devices can also be assembled together as a unit in a support base. A pumping mechanism or absorbent materials are preferably provided in the support base in order to remove the waste materials from the system. A group of twelve assay devices, each with eight ports form a microtiter arrangement in the support base and can be easily subjected to robotic or automated processing particularly with pressure pumping. In this regard, the present invention extends in the vertical direction of the volume of a microtiter plate and increases the usable surface area without increasing the horizontal area or footprint of a microtiter plate.

These and other features of the invention will become apparent from the following description of the invention, when viewed in accordance with the attached drawings and appended claims.

BRIEF DESCRIPTION OF THE DRAWINGS

FIGS. 4–6 illustrate another embodiment of an assay device in accordance with the present invention, with FIG. 4 being a perspective view of the device, FIG. 5 being a cross-section of the device, the cross-section being taken along lines 5—5 in FIG. 4, and FIG. 6 being an exploded view of the device.

FIG. 7 is a plan view of an alternate middle elastomer member for an assay device.

FIG. 8 is a plan view of a preferred embodiment of a middle member for an assay device.

FIG. 9 illustrates a support base for use with the present invention.

FIGS. 20–22 illustrate a preferred single sample assay device in accordance with the present invention, wherein FIG. 20 is a perspective view of the assay device, FIG. 21 is a cross-sectional view taken along line 21—21 in FIG. 20, and FIG. 22 is an exploded view of the device.

BEST MODE(S) OF THE INVENTION

Figure 1:
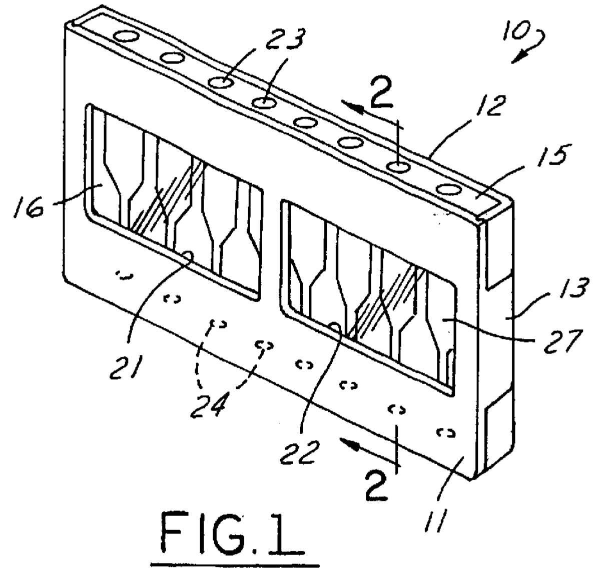
FIG. 1 is a perspective view of a preferred embodiment of an assay device in accordance with the present invention.
Figure 2:
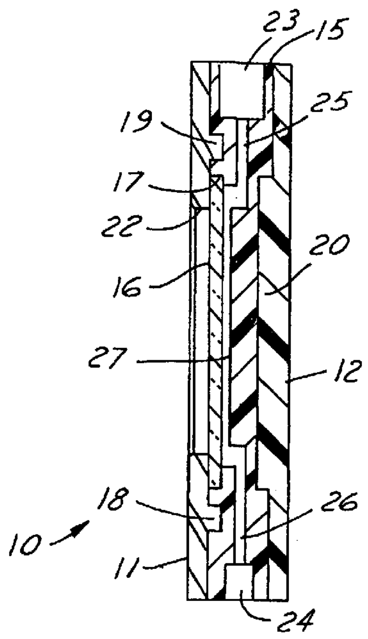
FIG. 2 is a cross-sectional view of the assay device shown in FIG. 1, the cross-section being taken along line 2—2 in FIG. 1.
Figure 3:
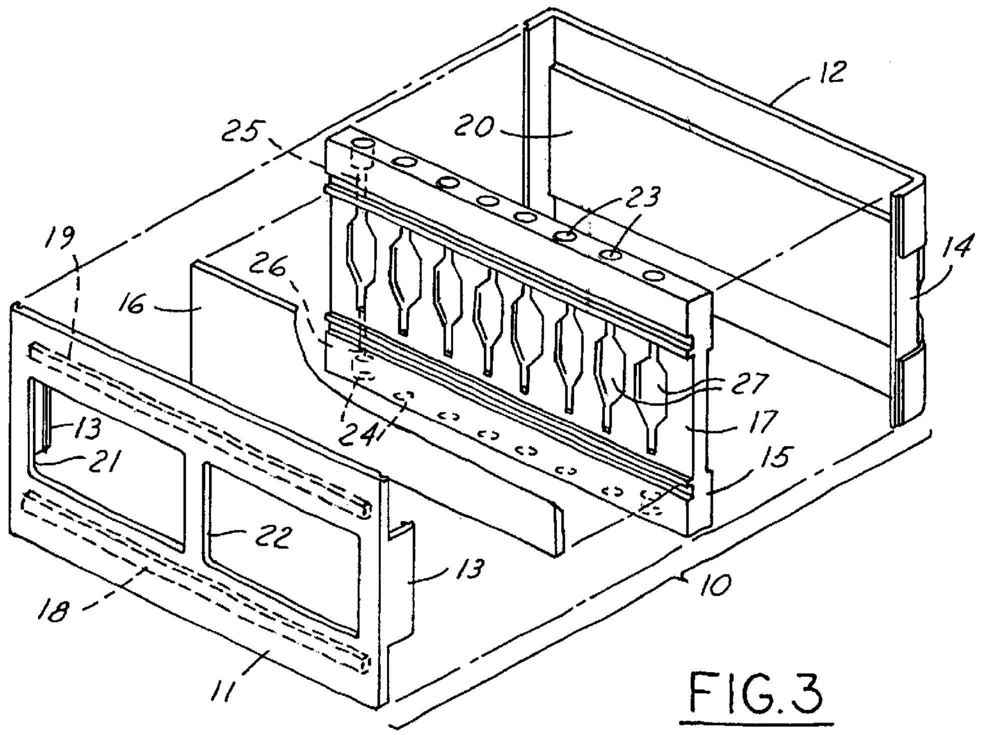
FIG. 3 is an exploded view of the assay device depicted in FIG. 1.

A preferred embodiment of a genetic assay device in accordance with the present invention is shown in FIGS. 1–3 and referred to generally by the reference numeral 10. The assay device is particularly adapted to allow determination of the presence or absence of Single Nucleotide Polymorphisms (SNPs) within a specific sequence of DNA. One of the attributes of the present invention is that it does not need to rely on complex automation in areas of liquid handling, device manipulation, and detection. For the most part, standard laboratory equipment can be used to perform an assay utilizing the present invention.

Once the assay is completed and the sample and reagent liquids have been removed, the internal slide member(s) is analyzed in some manner, such as by a fluorescence reader, densitometric or radioisotope systems, or the like. In this regard, the device can be disassembled and the other members can be discarded as biohazardous waste. Due to potential problems of contamination which could affect the analytical results, the present invention is preferably a low-cost disposable device which is discarded after a single use. Also, rather than disassembling the device partially or completely in order to read the spots on the glass slide(s), windows positioned on the sides of the assay device may permit reading of the slide(s) through them. One method for reading the spots includes slides by TIR (total internal reflection) using a laser light source.

Although the present invention has particular use in the detection of the presence or absence of SNPs relative to potential disease identification, the invention has numerous other uses for diagnostic applications. For example, the present invention can be used in pharmacogenomics and future drug development, including drug metabolism, toxicity and efficacy. For ease of description herein, the present invention will be described for use relative to disease-linked applications, but it is to be understood that the invention is not to be limited to such applications.

The assay device 10 consists of a two-piece housing comprised of a front member 11 and a rear member 12. The members 11 and 12 are preferably made from a plastic material, such as polyurethane, polycarbonate, or polystyrene, and are held tightly together by snap fit closure members 13, 14. A middle layer member 15 is held in place between the two housing members 11 and 12. The middle layer 15 is preferably made of a compliant, moldable elastomer member, such as polydimethysiloxane (PDMS) or liquid silicone rubber (LSR). PDMS is commercially available, for example, from Dow Corning under the brand name Slygard Elastomer 184, although other brands from other components could also be used. Both PDMS and LSR can be molded with precision and are compatible with the types of samples and reagent fluids used for DNA analysis. These materials also have an affinity to attach themselves to glass or any equivalent polished surface and form liquid-tight seals between the materials, and without bubbles. The adherence of such materials to glass is also reversible and they can be applied after the glass is silanized and arrays printed on it.

A glass slide member 16 is positioned in the housing and held in recess 17 formed in the middle layer. The slide member is spotted with arrays of oligonucleotides which are spotted and positioned on the slides in a conventional manner. The oligo arrays are designed to detect SNPs of interest. The slide member is preferably made of glass and can have a size and shape the same as standard microscope slides, although the invention is not limited to such members. The use of glass slides as substrates for the DNA arrays, however, provides easily available and inexpensive substrates, and also allows use of variety of reading, arraying and handling systems.

When the assay device 10 is assembled together, as shown in FIGS. 1 and 2, elongated ribs 18 and 19 on front housing member 11 and wide raised rib member 20 on the rear housing member 12, compress the middle layer and hold the glass slide 16 and middle layer 15 tightly in place. Windows 21 and 22 in the front cover members provide visual access to inspect the assaying process and also can allow reading of SNPs on the glass slide without disassembly of the device 10.

The middle layer 15 is preferably fabricated by a molding process and is formed with a plurality of inlet ports or openings 23, outlet ports or openings 24, micro channels 25 and 26, and recessed reaction or assay areas 27. A wide variety of widths, lengths, and depths of ports, channels and reaction areas can be utilized with the present invention. Preferably, eight inlet ports, reaction areas and outlet ports are provided in each assay device 10. This allows a group of twelve devices to be positioned in a support base, as discussed below, and be arranged in a microtiter format. The "pitch"or distance between the centers of the ports 23 is 9 mm. Of course, it is to be understood that the present invention is not limited to such number of ports and pitch dimension, any number and dimension can be utilized as desired.

The micro-sized channels typically range in diameter from 10 microns to 5 millimeters and more particularly from 50 microns to 1 millimeter. The micro-sized cavities typically have heights in the same range as the diameter of the micro-sized channels, and widths sufficient to encompass the arrays on the slide members.

With the present invention, it is unnecessary to provide separate sealing members, such as gaskets. Also, glues or other adhesives are not needed to secure and seal the components together. Additional layers could increase the size, expense, and complexity of the device. Also, the addition of adhesives or the like might constrict or block the small or micro-sized channels and recesses utilized in the invention.

In order to increase the amount of oligo arrays to be affected and the amount of SNPs to be detected, two glass slide members could be provided in the housing, one on either side of the middle member. For this embodiment, two sets or rows of recessed reaction sites would be provided on the middle layer, one set or row on each side. Another set of windows could also be provided on the rear housing member.

Figure 6:
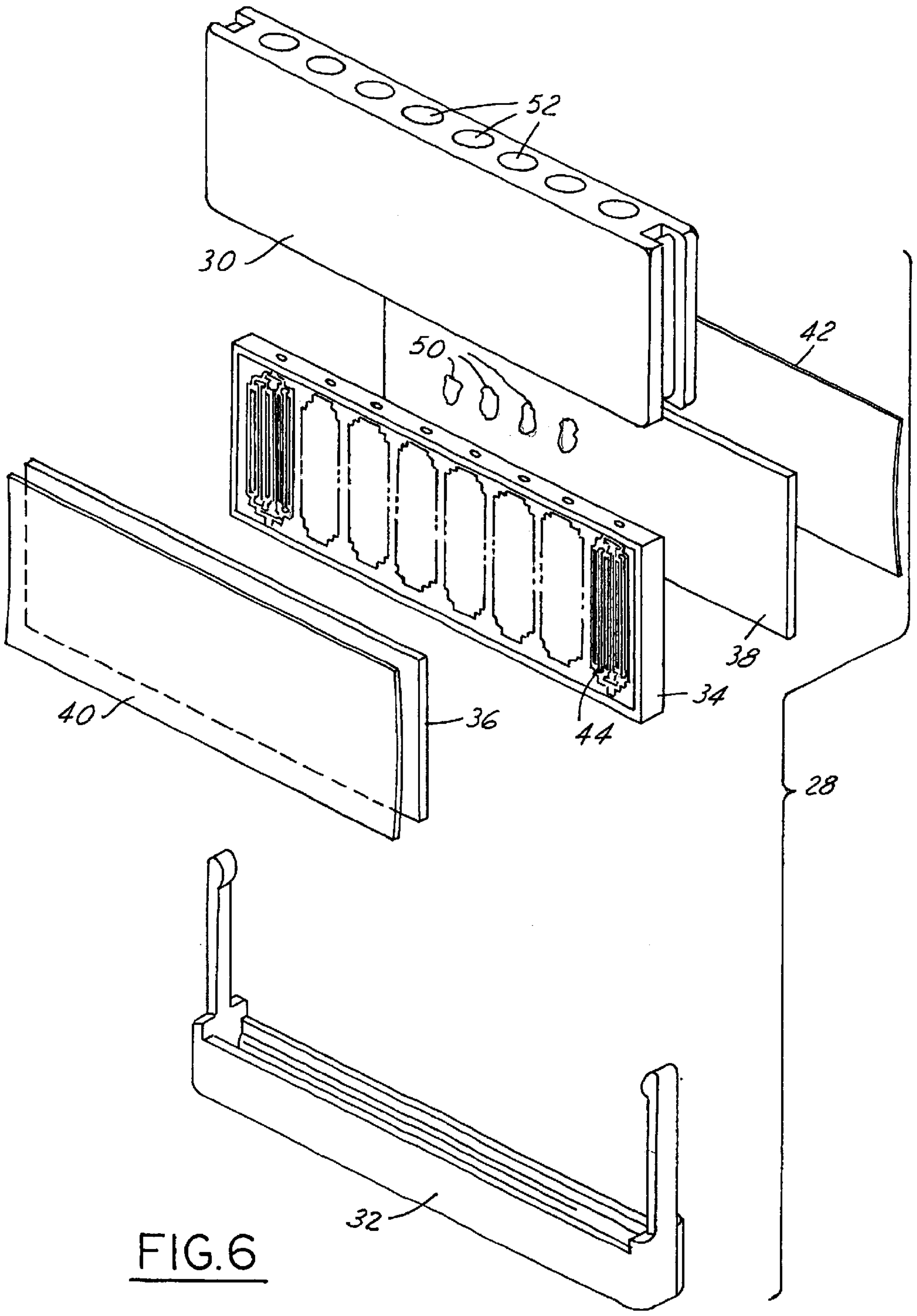

An embodiment of the invention which includes two glass slide members is shown in FIGS. 4–6 and identified by the reference number 28. The assay device 28 has a two-piece body or housing, a pair of glass slide members, an elastomer middle layer and a pair of resilient members which help hold the device together. The body of the device 28 consists of a U-shaped housing member 30 and a frame member 32 which are snap-fitted together. Preferably, the two members 30 and 32 are made from a plastic material and held together by internal clip-type features of standard design. Positioned within the device or housing are a middle layer 34, two slide members 36 and 38, and two biasing members 40 and 42.

The middle layer 34 is preferably made of a PDMS, LSR or an equivalent material which is compatible with the type of samples and reagent fluids used for DNA analysis. The elastomer material also conforms to the glass slides 36 and 38 and creates a liquid tight seal against them.

The middle layer 34 is similar to middle layer 15 discussed above and preferably is fabricated by a molding process with one or more recessed reaction cavities 44. In this regard, the cavities 44 can have a series of channels as shown in FIGS. 6 and 7, or can comprise one open channel 44' as shown in FIG. 8. As indicated above, a wide variety of widths, lengths, and depths of reaction cavities can be utilized with the present invention. The number and arrangement of the cavities also is discretionary and dependent on a number of factors. The two embodiments shown in FIGS. 7 and 8 are simply representative of the wide varieties which can be utilized, and are not meant to be limiting.

In the assay device 28, two slide members 36 and 38 are provided. The slides are made of glass and preferably are the size and shape of a standard microscope specimen slide. Each of the slide members contains areas or sites 50 (see FIG. 6) that comprise arrays of deposited oligonucleotides. The oligo arrays can be designed to detect SNPs of interest. The number of SNP tests per device depends on the design of the cavities and the density of the array.

When the assay device 28 is assembled, as shown in the cross-section in FIG. 5, the two curved biasing members 40 and 42 are inserted into the housing member 30. These biasing members are preferably curved plastic "springs" and apply a constant slight pressure to the slide members 36 and 38. This provides stability to the entire assembly and also helps provide a liquid-tight seal between the PDMS middle member 34 and the glass slide members 36 and 38. In the alternative, it is also possible to utilize ribs or other features on the housing which provide compression forces on the slides and/or middle members, as shown above with reference to FIGS. 1–3.

It is also obvious to persons skilled in the art that only one biasing member might be utilized, or that alternate equivalent types or systems of biasing mechanisms could be utilized.

After the housing member 30, middle layer member 34, glass slide members 36 and 38, and biasing members 40 and 42 are assembled together, the second housing (frame) member 32 is snapped into place. In this regard, members 30 and 32 can contain internal chamfers that help locate the slide members, middle layer and biasing members during assembly.

Rather than have the openings in the middle layer be exposed for direct access to manual or automatic loading mechanisms (as shown in FIGS. 1–3), a plurality of openings or ports 52 can be provided in the housing member 30. These ports provide direct access to each of the channel members 44, whether they are open channels or a series of smaller channels as shown in FIGS. 6 and 7. In addition, corresponding openings 54 (shown in FIGS. 5 and 6) are provided in the second housing (frame) member 32 in order to allow liquids to exit from the assay device 28. Preferably, eight ports 52 and eight ports 54 are provided.

When assembled, the middle layer 34 is in slight compression by the other members of the device. Also, a raised ridge or boss surrounds each inlet and outlet port. The bosses press into the middle layer providing individual seals to each port.

Similar to assay device 10, the assay device 28 also is preferably disposable and thus discarded after use. Thus, the assay devices are assembled just once, during manufacturing. The housing components 11, 12 and 30, 32 contain interlocking features that allow for disassembly once the assay is complete. After disassembly, the slide members are sent for further processing, while the remaining portions of the device are discarded. In this regard, the other portions of the assay devices can be discarded as biohazardous waste.

The slides are subsequently analyzed in a standard manner, such as by a "fluorescence reader" or by any other conventional analytical system. The assay results can also be read by eye, color, or a laser reader. A CCD camera or PC scanner could also be used to record the results.

In order to test a large number of SNPs at the same time, a plurality of assay devices 10 or 28 can be positioned in a support base 60, as shown in FIG. 9. The support base 60 has a recess or well 62 in which a plurality of assay devices are positioned, as well as a console control and readout section 64.

Preferably, support base 60 holds up to twelve assay devices 10, 28. When fully loaded, the inlet ports of the devices are in the same configuration as a 96-well microtiter plate. The 96-well configuration of the inlet ports allows for the presentation of sample and reagents to the devices by standard fluid handling and dispensing systems that are typically found in laboratories. In essence, the present invention extends a microtiter plate in the vertical direction which increases the usable surface area without increasing the footprint of the plate.

Samples or reagents are added to the assay devices 10, 28 through the inlet ports 23 and 52. This can be accomplished either manually or automatically. After appropriate incubation where required, products are extracted through the outlet ports 24, 54 on the bottom or opposite side of the devices, as defined by DNA and SNP protocol.

Purified DNA samples are dispensed into the inlet ports of the assay devices. The dispensing can be performed either manually, such as by use of hand pipetters, or automatically, such as by use of equipment such as the TECAN Miniprep, Genesis or BioMek liquid handling devices. Seals between the assay devices 10, 28 and the support base 60 along with the closed fluidic system within the support base prevents the samples from prematurely entering the cavities of the device.

At a control point, the fluidic system within the support base causes the samples to enter and fill the cavities of the assay devices. Once the samples are no longer needed, they are drawn or forced out of the devices 10, 28 and into a waste management section of the support base. Wash and other reagents are then presented to and extracted from the devices in a similar manner. The triggering of these fluidic operations is done either manually or automatically through computer control, depending on the design of the support base.

The support base 60 controls the flow of fluids in and out of the assay devices 10, 28 and provides waste management. The outlet ports of each assay device are connected to a common fluid line within the support base 60. A pumping mechanism of some type, such as a peristaltic pump, syringe pump, or other similar device, controls the fluid flow in each line. The lines are maintained separately between the assay devices and the pump. This also allows support base 60 to be partially populated with devices. Thus, a full complement of assay devices is not needed in order to utilize the support base 60. After the pumping operation is finished, the lines may be joined into common lines or run separately to a waste management system. The waste management system may consist of a waste container, a laboratory waste system, or any other appropriate method of disposal of such materials.

In the alternative, it is also possible to simply provide an absorbent material in the well 62 which collects and absorbs the materials exiting the assay devices. Pressure heads could also be positioned in contact with the assay device inlet ports and pressure pulsing or pumping could be utilized to flow the DNA, reagents and other materials through the assay devices. If desired, capillary breaks could be provided in the outlet ports in order to hold the materials in the reaction recesses until it is desired to allow them to exit. Pulses of pressure could be utilized to break the capillaries.

The assay analysis requires that fluid operations be performed at precise times as defined by appropriate DNA protocol. Thus, the support base 60 should contain both manual and automatic methods for controlling fluid operations. In this regard, the support base should contain switches, buttons, or other devices for manually initiating fluid operations. An electro-interface, such as an RS232 connection, can provide for computer-controlled initiation of fluid operations in sync with pipetting operations that may be performed by external laboratory automation devices.

A semi-automated operational mode is also possible. This is appropriate when the pipetting steps are manually performed. Through an RS232 interface, the assay protocol can be downloaded into the support base 60. Through the use of audible signals, visual indicators, and textual prompts on an internal LCD (liquid crystal device), the user of the device can be prompted to perform each step in the protocol. Once completed, the control system in the support base performs the appropriate fluidic operations.

In operation as a practical matter, the middle layers 15, 34 can be optimized for specific applications. Each configuration would affect items such as throughput, cost per SNP result, the amount of reagent volumes utilized, and the like. For example, the area of the reaction recesses 27, 44 can be 14 mm by 19 mm and the depth of the cavity 0.5 mm.

The spotting densities can have a spot density, such as 300 μm diameter spots on 500 μm centers. This gives a nominal spot density of four spots/$mm^2$. A higher spot density could have 500 μm diameter spots on 100 μm centers, giving a nominal spot density of 25 spots/$mm^2$. In general, it is believed that an assay or analysis using the present invention can be performed in three hours or less.

With use of a support base and automated equipment, the present invention can be used as part of a high-throughput system for conducting massive SNP genotyping. This can enable scientists and researchers to rapidly analyze SNPs and their role in disease and drug efficacy. It can also help scientists to better understand the role of genetic variation in disease and drug response.

Figure 10:
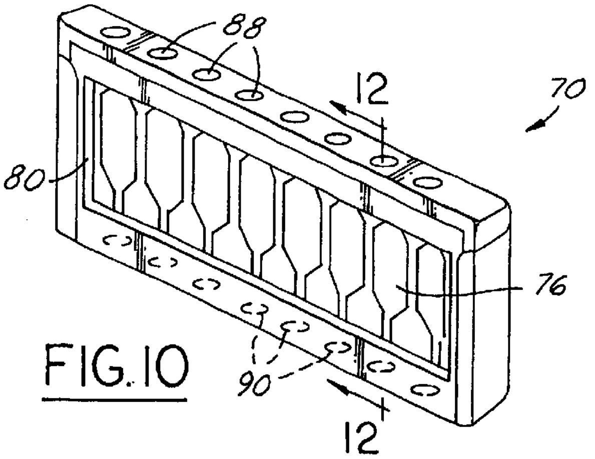
FIGS. 10–12 illustrate an alternate embodiment of an assay device in accordance with the present invention, with FIG. 10 being a perspective view, FIG. 11 being an exploded view, and with FIG. 12 being a cross-sectional view of the assay device shown in FIG. 10, the cross-section being taken along line 12—12 in FIG. 10.
Figure 12:
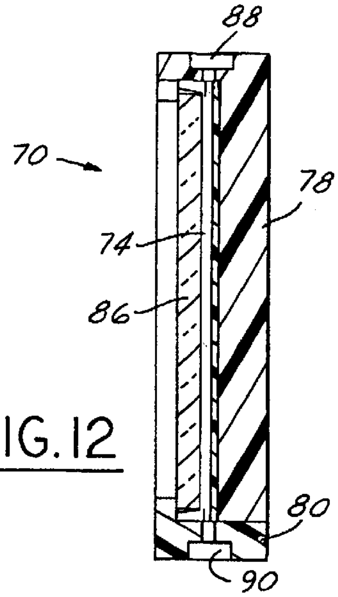
Figure 11:
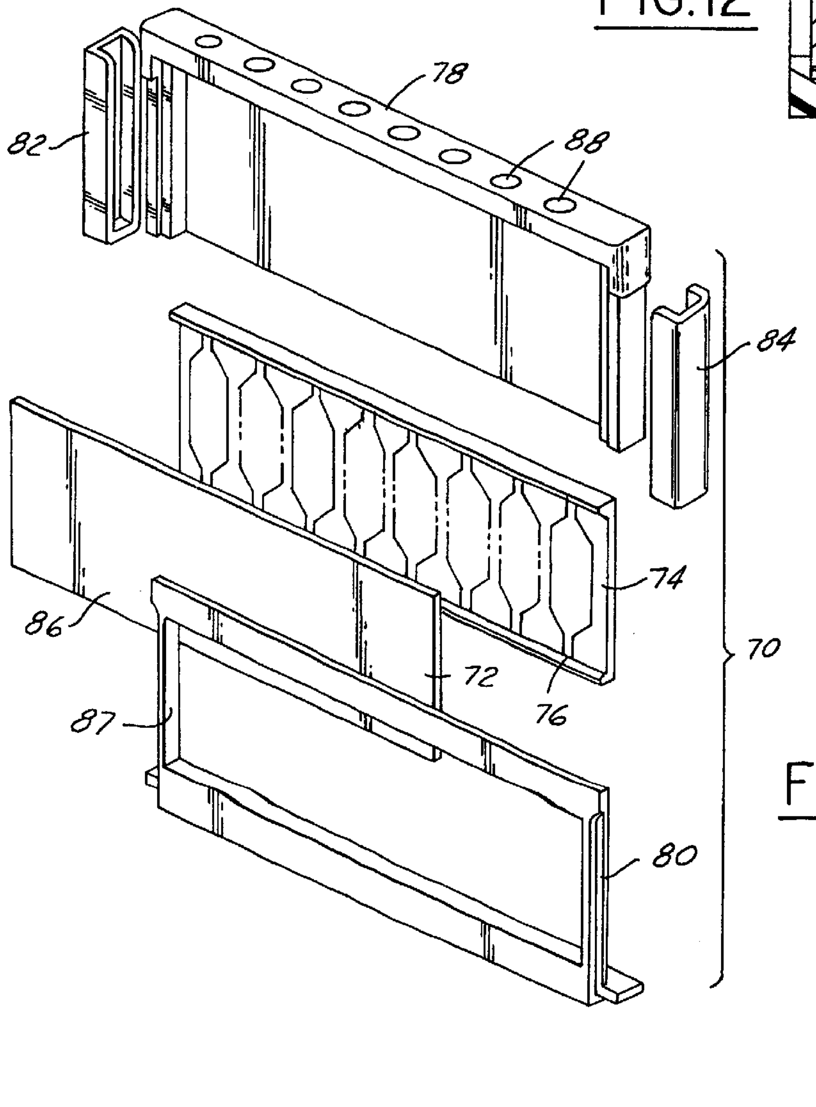
Figure 13:
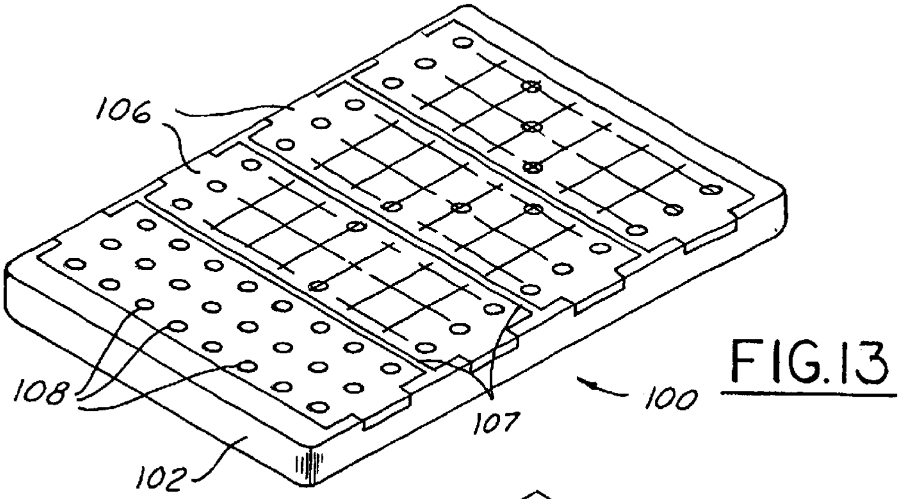
FIGS. 13–16 illustrate still another embodiment of an assay device in accordance with the present invention, with FIG. 13 being a perspective view, FIG. 14 being an exploded view, FIG. 15 being a top plan view, and FIG. 16 depicting one of the top plate members.
Figure 14:
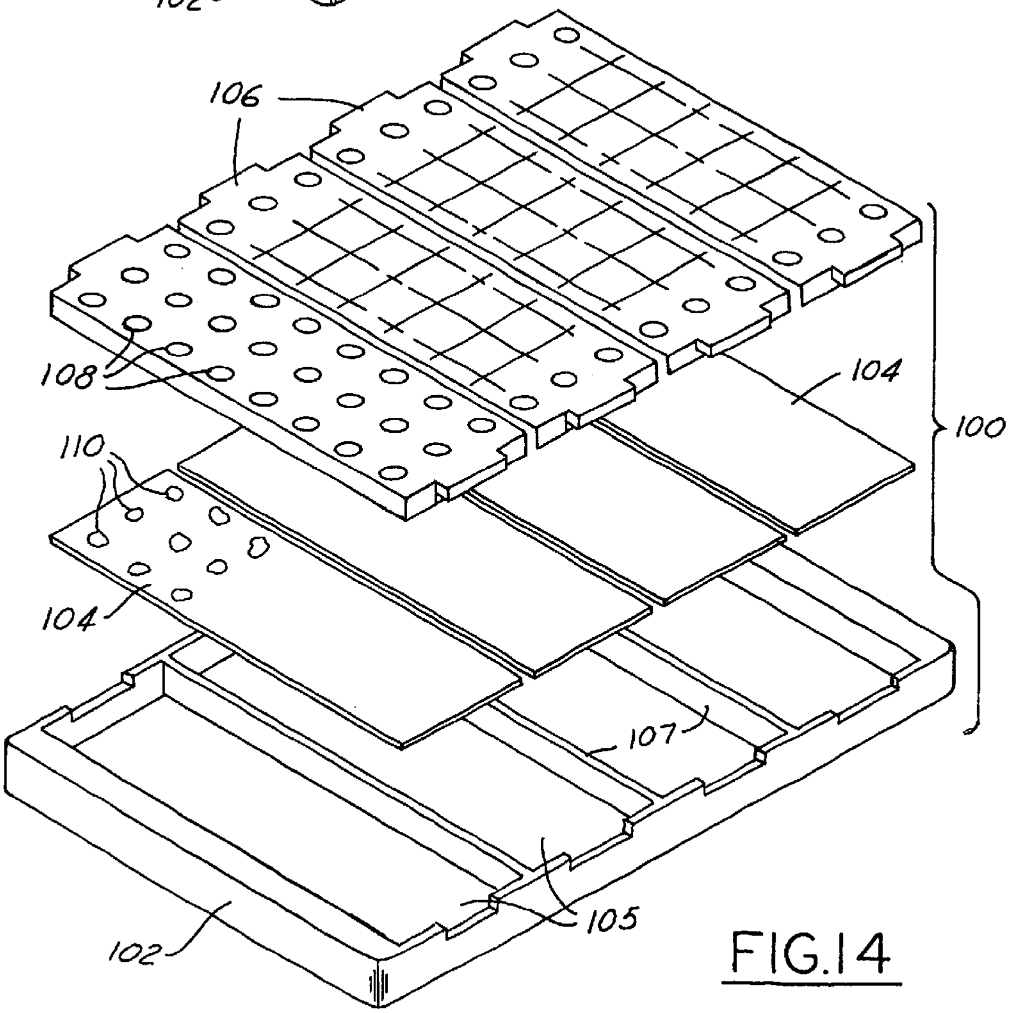
Figure 15:
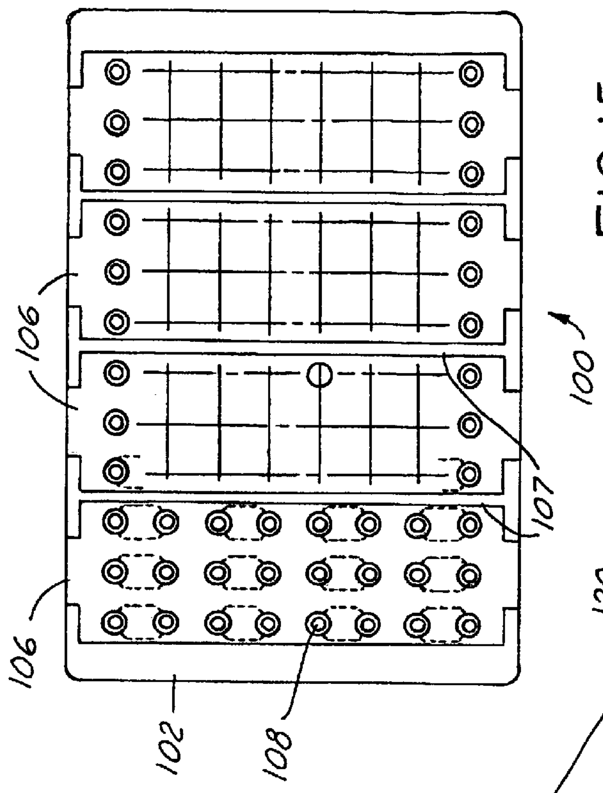
Figure 16:
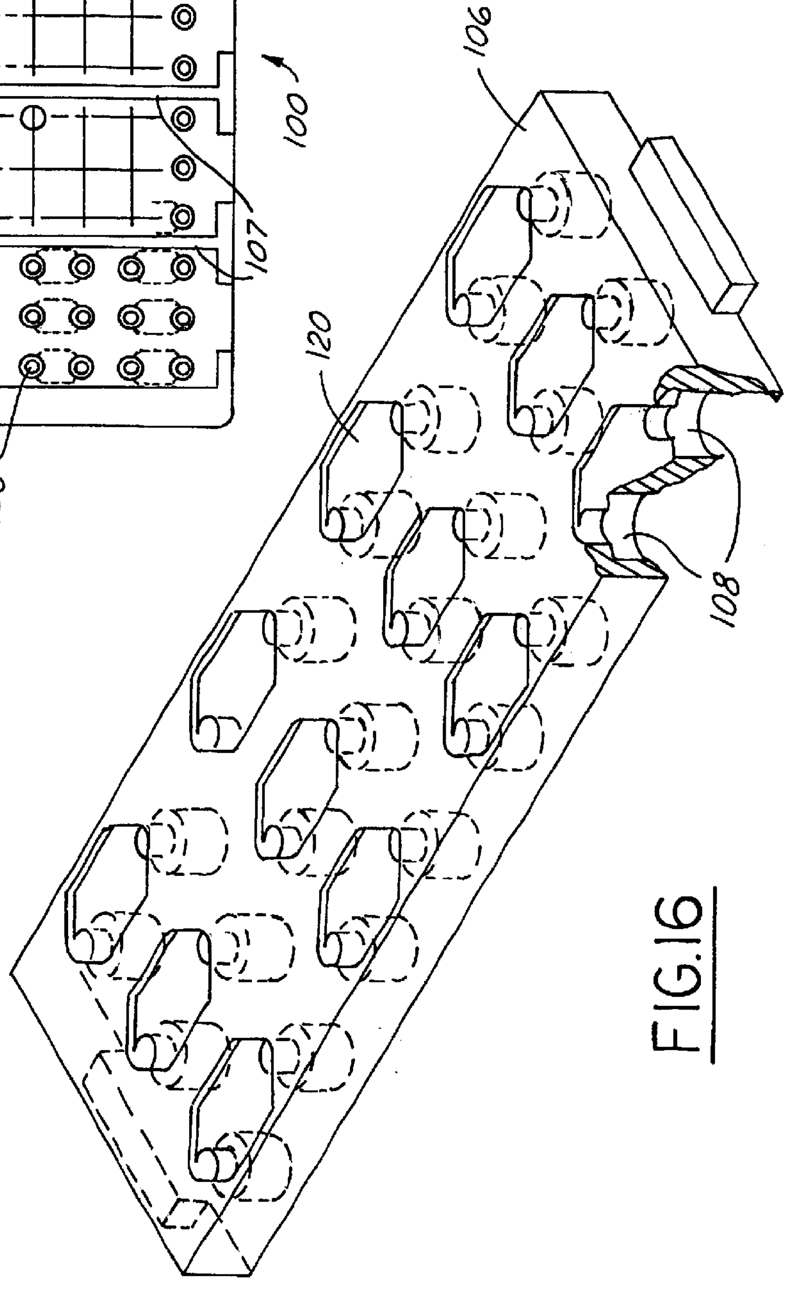

Another alternate embodiment of an assay device for use in the present invention is shown in FIGS. 10–12. This device is identified by the reference numeral 70. Similar to assay device 10, the device 70 only has one glass slide member 72, and the middle layer 74 only has fluid channels 76 on one side.

The glass slide member 72 and middle layer 74 are positioned in a housing member 78 which is positioned on a frame member 80 and held in place by two end members 82 and 84. One side 86 of the glass slide member 72 provides a window or viewing access into the interior of the assay device 70 when it is assembled. Opening or window 87 is provided in frame member 80 for this purpose. The access for observation also allows SNPs on the glass slide member to be detected by conventional equipment without disassembling the device.

Similar to the assay devices 10 and 28, the assay device 70 has a series of ports or openings 88 in the top surface and a series of corresponding ports 90 in the lower surface. Again, preferably eight ports 88 and 90 are utilized in the device 70 so that a group of twelve devices 70 can be positioned in a support base, such as support base 60 described above with reference to FIG. 6, and utilized in a 96-well microtiter plate configuration.

Another embodiment of an assay device 100 which can be used with the present invention is shown in FIGS. 13–16. This device includes a base member 102, a plurality of glass slide members 104, and a plurality of apertured cover plate members 106. The cover plates 106 have a series of openings 108 in them which open onto the oligo arrays 110 positioned on the glass plate members 104. Each pair of ports or openings 108 is connected to a single reaction recess 120. The plate members 106 can be made of an elastomer material, such as PDMS or LSR, in order to provide a tight seal on the glass slide members 104, or a separate gasket member (not shown) can be provided between the plate members 106 and slide members 104 for that purpose. With the assay device 100, forty-eight separate assays can be performed simultaneously, producing four glass slides 104 for subsequent analysis. Of course, as indicated earlier, the present invention is not limited to devices or systems having certain sizes or numbers of ports, assay sites and the like. For example, one large (e.g. 80×120 $mm^2$) glass slide could be provided.

The tray member 106, holds four plate members 106 and four glass slide members 104. The plate members fit within recesses or segregated areas 105 in the tray 106, the segregated areas being separated by wall members 107.

Figure 17:
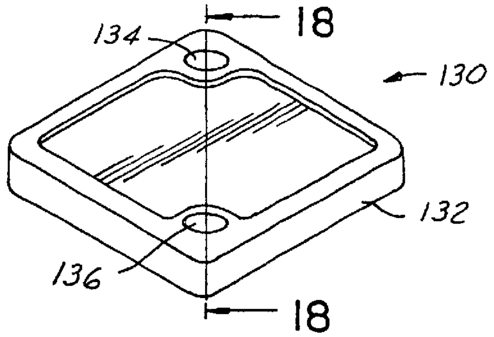
FIGS. 17–19 illustrate a single sample embodiment of the present invention, with FIG. 17 being a perspective view, FIG. 18 being a cross-sectional view taken along line 18—18 in FIG. 17, and FIG. 19 being an exploded view.
Figure 18:
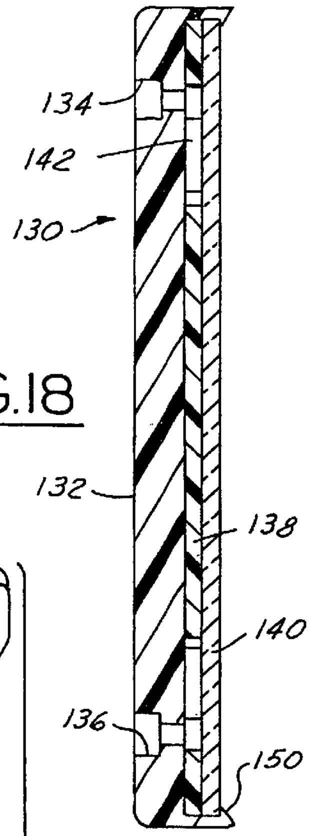
Figure 19:
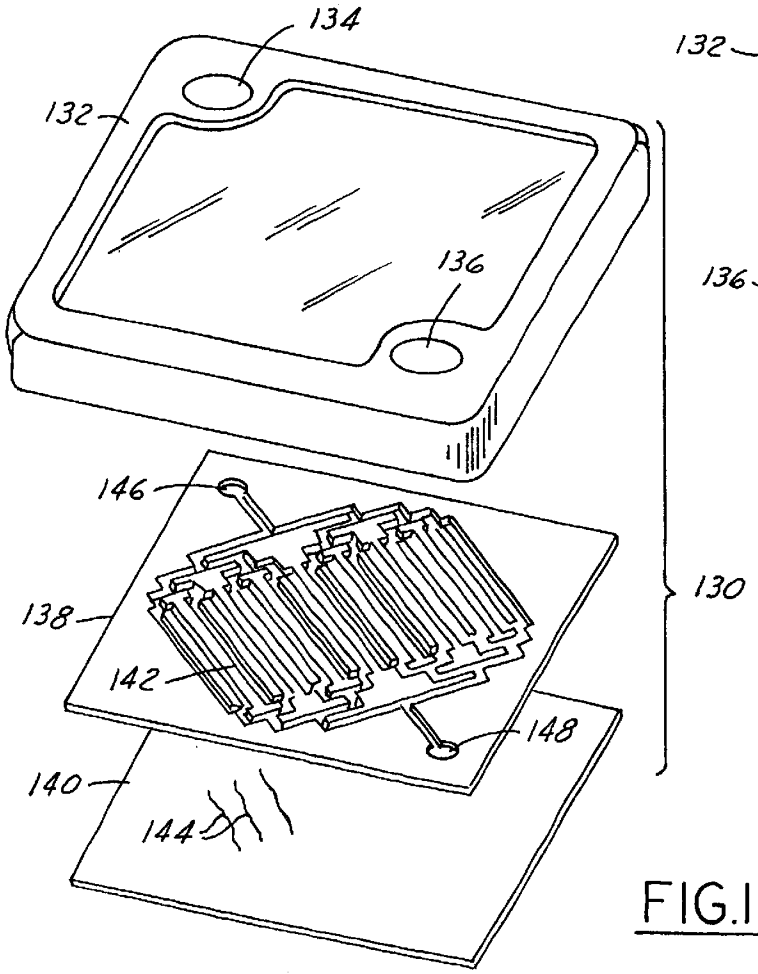

A single sample assay device 130 is shown in FIGS. 17–19. Device 130 includes a molded plastic housing member 132 with a pair of openings 134 and 136, a middle elastomer layer 138, and a bottom glass slide member 140. The middle member 138 has a plurality of slots or channels 142 which are positioned and arranged in order to allow liquids to have access to spots of oligo arrays 144 positioned on the glass slide member 140. The slots or channels 142 are accessed by the fluids from centralized openings 146 and 148 which are aligned with openings 134 and 136, respectively, in housing member 132.

The middle layer 138 and glass slide member 140 are held in the housing by overlapping members 150 positioned on at least two opposed edges of the housing member 132. Once the assay device 130 is utilized, the apparatus is disassembled and the glass slide member 140 retained for subsequent analysis.

Figure 20:
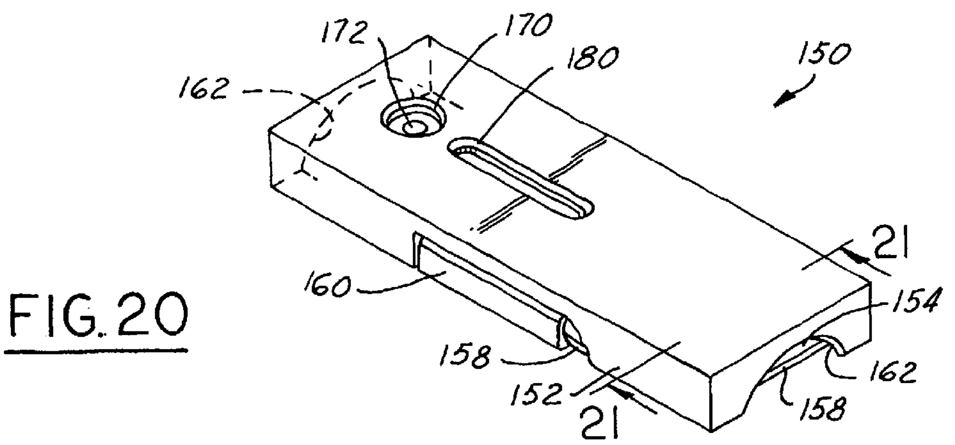
Figure 21:
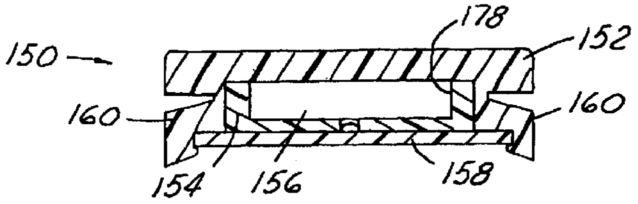
Figure 22:
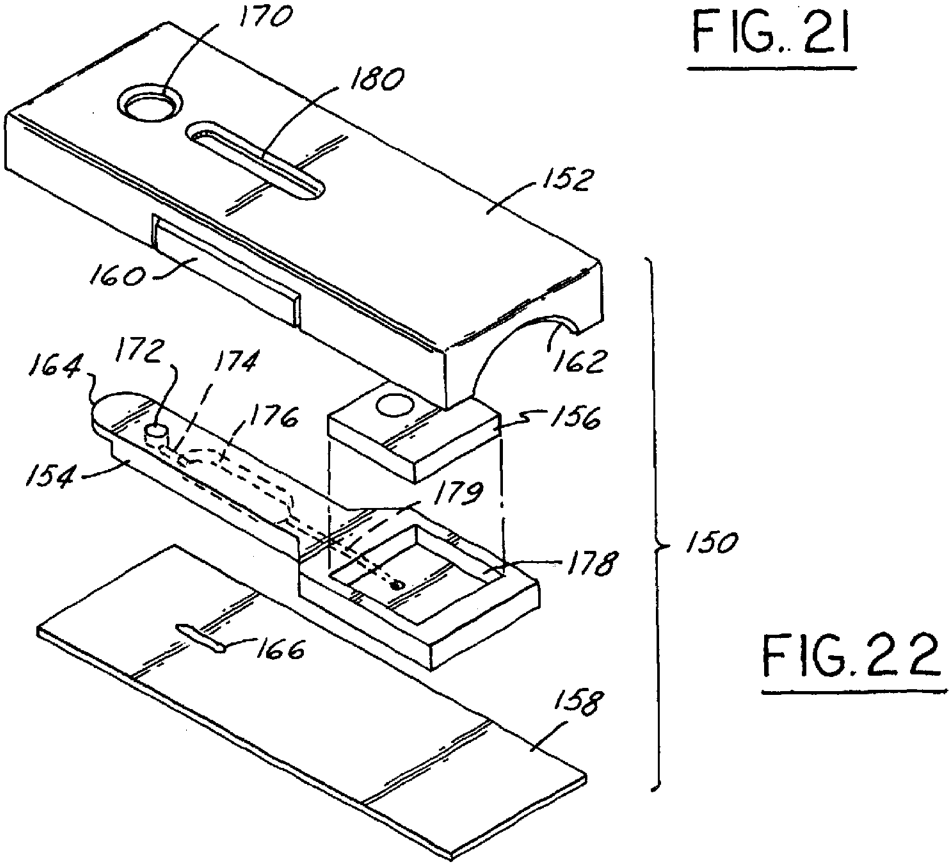

A preferred embodiment of a single sample assay device in accordance with the present invention is shown in FIGS. 20–22 and referred to by the reference numeral 150. The assay device 150 includes a housing or cover member 152, an elastomer member 154, an absorbent member 156, and a glass slide member 158. When the device 150 is assembled, hinged latch members 160 are used to hold the various parts in place and tightly together. The housing or cover member 152 is snapped over the glass slide member 158. When it is desired to disassemble the device 150, openings 162 allow manual grasping of the slide member with one hand while the cover member 152 is removed with the other hand.

The elastomer member 154 is preferably made from PDMS or LSR, as discussed above. These materials seal tightly against the glass slide member providing a liquid tight seal. When it is desired to remove the elastomer member 154 from the glass slide member 158, the tab member 164 can be grasped so that the member 154 can be peeled away from the glass slide member. Thereafter, the oligo arrays 166 on the glass slide 158 can be analyzed for the presence or absence of SNPs. (In the alternative, as mentioned above, the glass slide member could be analyzed without complete disassembly of the device.)

The cover member 152 has an opening or port 170 which aligns with opening or port 172 in the elastomer member 154. DNA, reagents, wash materials and the like are introduced into the assay device 150 through ports 170 and 172. Small micro channel 174 formed in the bottom of elastomer member 154 conveys the materials to reaction recess 176 which is positioned over the spots of oligo arrays 166. Window 180 in cover member 152 allows visual inspection of the passage of the materials through recess 176 during the assay process.

An absorbent member 156, such as a small pad or sponge, is positioned in the cavity 178. The absorbent member 156 soaks up the excess DNA, reagents and wash materials which are introduced into the device and passed over the arrays 166. Microchannel 179 conveys these materials from the reaction recess 176 to the cavity 178. The absorbent material takes up only excess fluid exiting the array cavity or recess, and is prevented from completely draining the chamber by means of the separating channel or void. The single sample device is disposable. Once the assay is completed, the housing (cover member) 152, elastomer member 154 and absorbent member 156 can be discarded.

Figure 23:
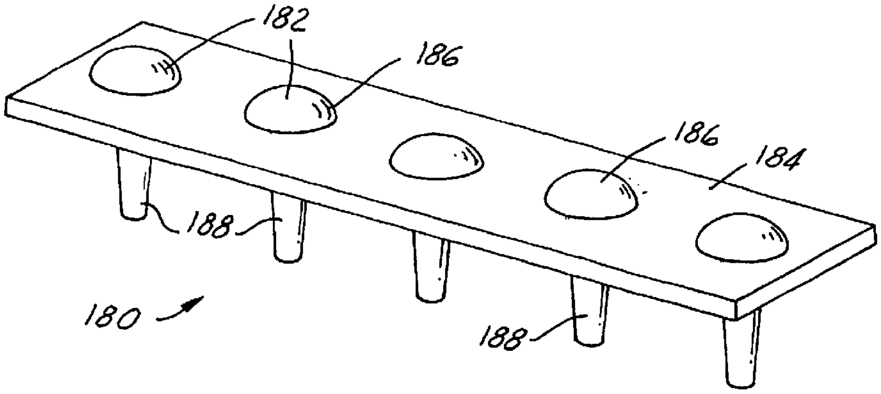
FIG. 23 is a dispenser device which can be utilized with the present invention.

One manner in which the DNA samples, reagents and/or wash materials can be introduced into the assay device 150 is with a dispenser device (or reagent card) 180, as shown in FIG. 23. The dispenser device has a plurality of small volume storage containers 182 in a plate member 184, the containers covered by "bubble pack" or "blister pack" modules 186. Nozzles 188 are positioned below each of the containers 182 and are sized and adapted to be inserted into ports or openings 170, 172 in the assay device 150. Each of the containers 182 is filled with a small volume of a DNA sample, reagent or wash fluid.

When it is desired to synthesize the oligo arrays spotted on the glass slide member 158, an appropriate nozzle 188 is positioned in port 170 and the bubble 186 is pushed down toward the plate member 184 forcing the liquid material into the assay device 150. In this manner, the oligo arrays 166 can be easily and quickly subjected to the principal DNA samples or reagents.

The present invention provides an improved assay and analytical device, process and system, which is faster to use and less expensive than known DNA assay devices. Also, due to the minute size of the channels and reaction recesses, only small amounts of reagents, DNA samples, etc. are utilized. Again, this saves expense.

The present invention is also versatile and can be used for various analytical processes and can be used with array formats of virtually any size or number, such as 96, 384 or 1536. The invention also allows use of an analytical device which has a microtiter format and can be used with standard laboratory equipment.

Figure 24:
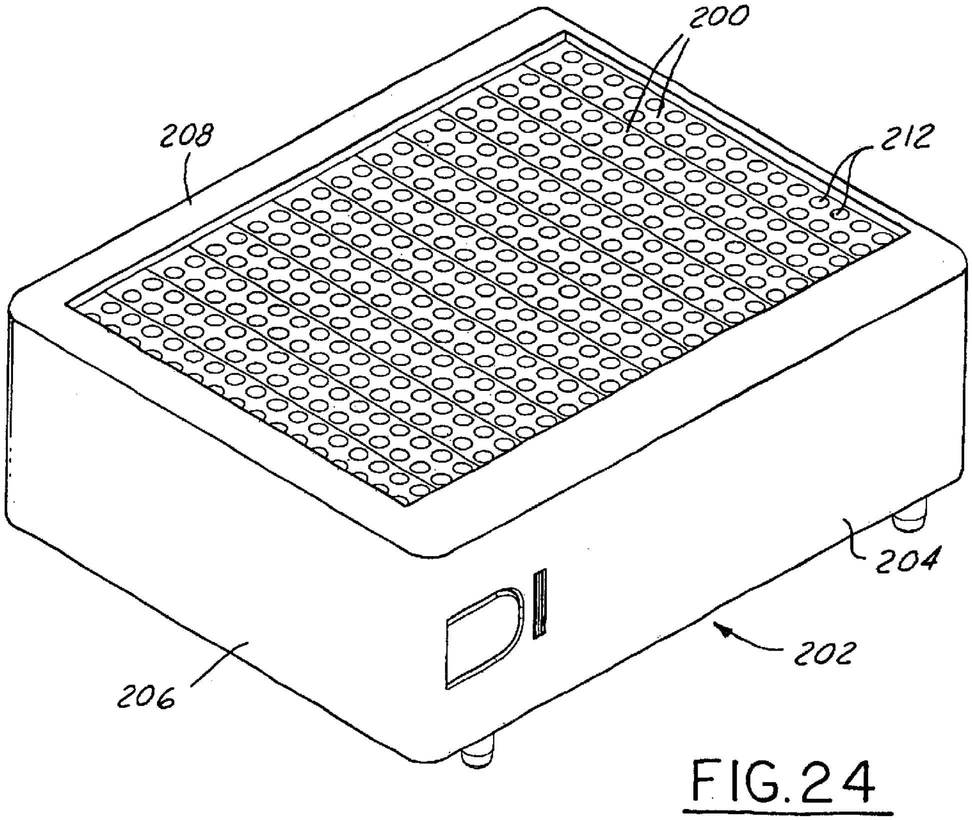
FIGS. 24 and 25 illustrate a group of sample synthesis devices assembled and held together in a frame mechanism, with FIG. 24 being a perspective view and FIG. 25 being an exploded view.
Figure 25:
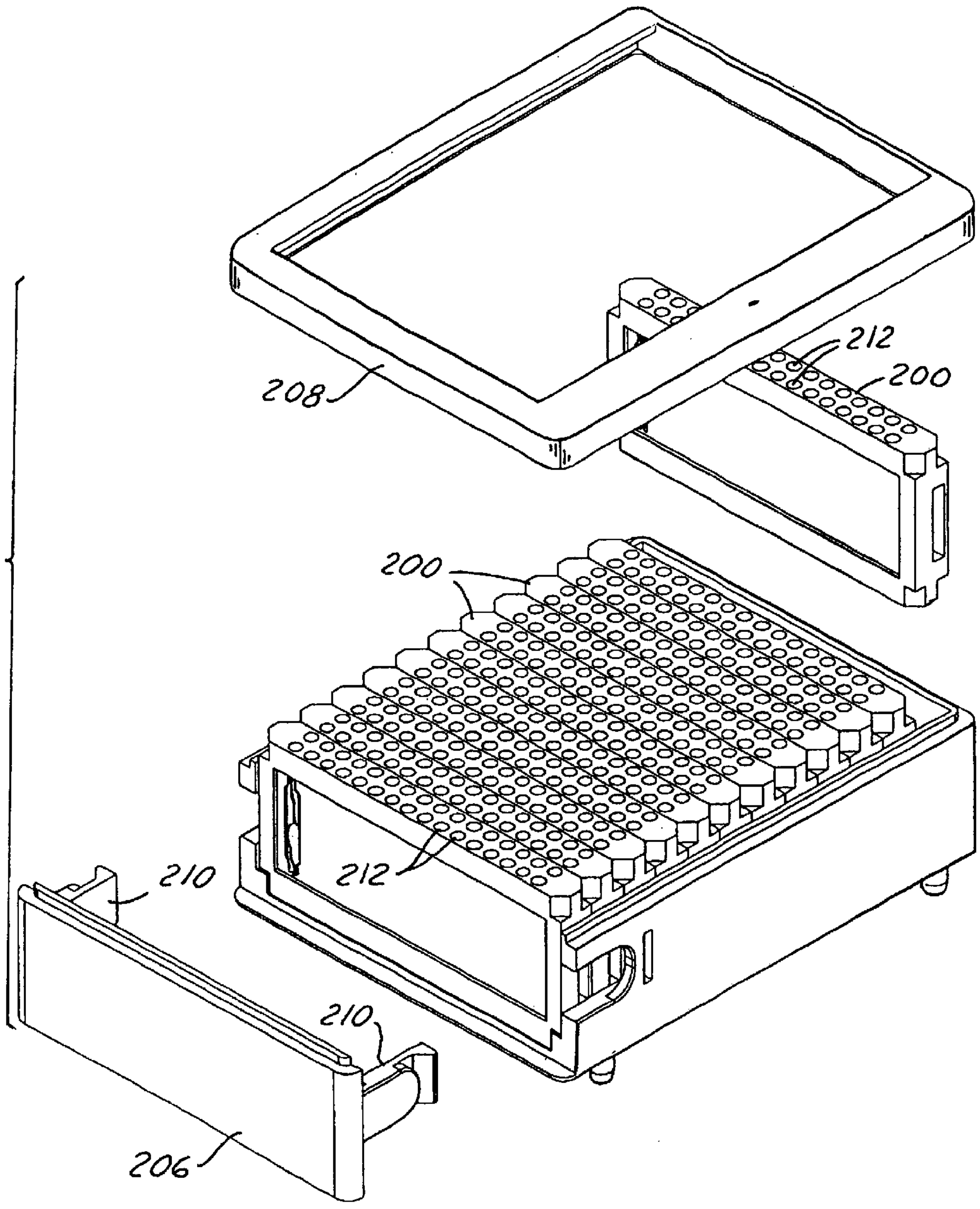

FIGS. 24 and 25 illustrate a group of sample synthesis devices 200 which are assembled and held together in a frame mechanism 202. The frame mechanism includes a base member 204, a front cover member 206 and a top frame member 208. The cover member 206 is snap fit together with the base member 204 by a pair of latch members 210. A plurality of synthesis devices 200 are positioned in the base member. Preferably each of the devices 200 have thirty-two openings or ports 212 positioned in two rows of sixteen ports each, and preferably the base member is adapted to hold twelve devices 200. This arrangement provides a 384-opening format (16×24) which then can be used with automated or robotic processing systems.

The devices 200 are preferably provided with a construction and assembly similar to devices 10, 28, and/or 70 set forth and described above. In this regard, one or two glass slide members are provided in each device 200, together with a conformable molded elastomer middle layer and a plastic housing. Microchannels and reaction recesses are also provided in the middle layer in communication with the ports 212.

Figure 26:
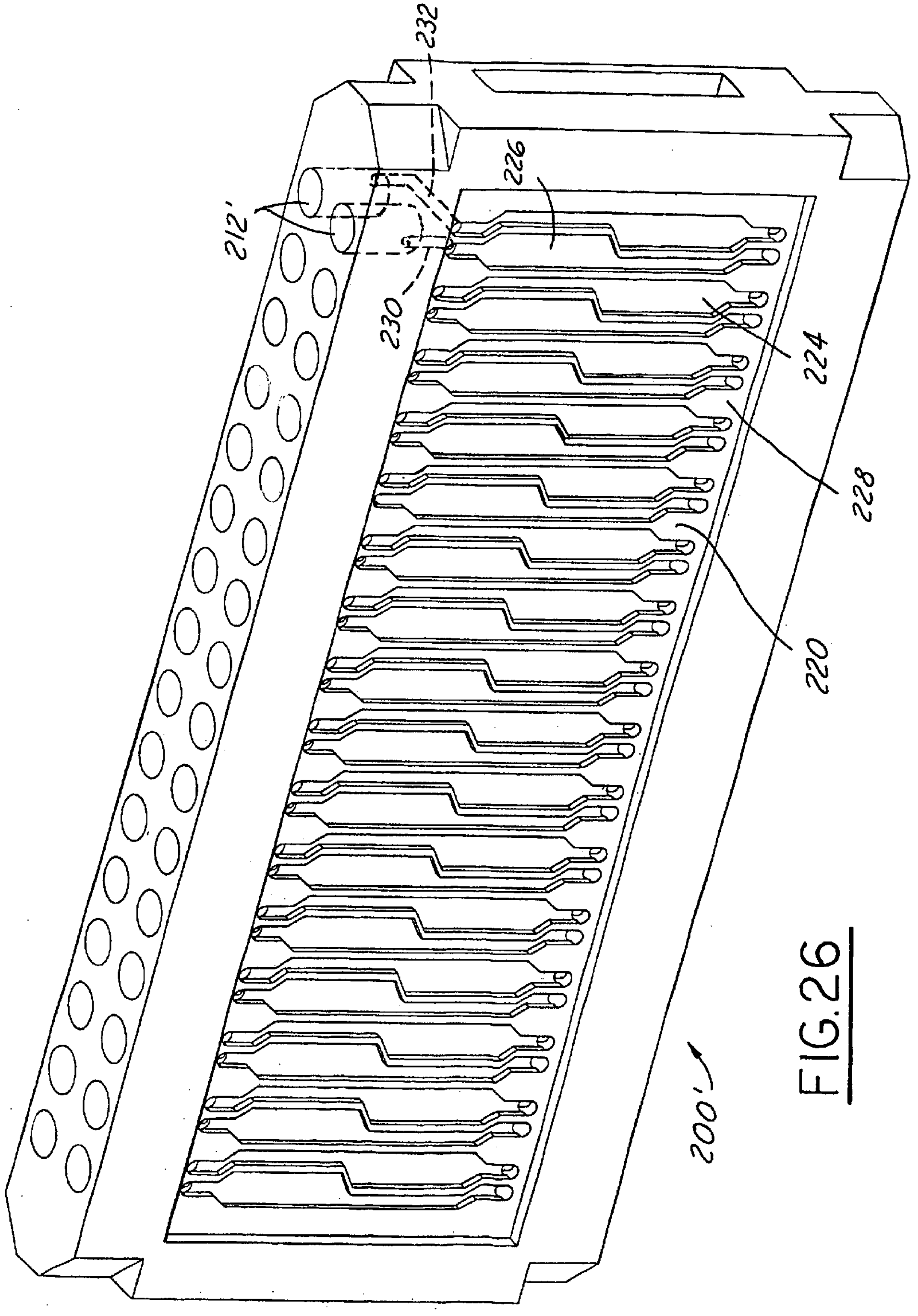
FIG. 26 illustrates still another embodiment of a sample assay device in accordance with the present invention.

A device 200' which utilizes a single glass slide member 220 is depicted in FIG. 26. Each of the ports 212' are provided in communication with reaction recesses 224, 226 on the same side of the middle layer 228. Appropriate channels 230, 232 are provided for this purpose. With the device 200', all of the oligo arrays to be synthesized can be positioned on the same side of one glass member which can simplify the subsequent detection and analysis procedures.

While particular embodiments of the invention have been shown and described, numerous variations and alternate embodiments will occur to those skilled in the art. Accordingly, it is intended that the invention be limited only in terms of the appended claims.

What is claimed is:

1. A analysis device comprising:

a housing;

at least one glass slide member positioned in the housing;

an elastomer member positioned in said housing and said housing urging said elastomer member into sealing arrangement with said at least one glass slide member, said elastomer member having at least one channel thereon, at least one inlet port and at least one outlet port;

wherein materials entering said housing through said at least one inlet port are transported through said at least one channel and out through said at least one outlet port.

2. The analysis device as claimed in claim 1 wherein a plurality of inlet ports and a plurality of outlet ports are provided in said elastomer member.

3. The analysis device as claimed in claim 1 wherein two glass slide members are provided, one positioned on each side of said elastomer member, and wherein said elastomer member has at least one channel on each side.

4. The analysis device as claimed in claim 1 wherein said elastomer member provides a liquid tight seal on said glass slide member without the need for adhesives, gaskets or other sealing members between the glass slide member and the elastomer member.

5. The analysis device as claimed in claim 4 wherein said elastomer member is made from a material selected from the group comprising polydimethylsiloxane (PDMS), liquid silicone rubber (LSR) or other elastomeric material having an inherent sealing affinity.

6. A system for analyzing materials comprising:

at least one analysis device and a support base, (a) said analysis device comprising:

(i) a housing;

(ii) at least one glass slide member positioned in the housing;

(iii) an elastomer member within said housing, said housing urging said elastomer member into a sealing arrangement with said at least one glass slide member, said elastomer member having at least one channel thereon, at least one inlet port and at least one outlet port;

(iv) wherein materials entering through said at least one inlet port are transported through said at least one channel and out through said at least one outlet port, and (b) said support base comprising a housing having a control portion and a recess, said recess having space for a plurality of analysis devices, and said control portion having a mechanism for eliminating waste materials ejected from said analysis devices.

7. The system as claimed in claim 6 further comprising evaluation means for inspecting said at least one slide member.

8. A device comprising:

a housing having a first portion and a second portion, said first portion engaging said second portion;

at least one glass slide member positioned between the first housing portion and the second housing portion;

an elastomer member positioned between said first housing portion and said second housing portion so that when assembled said first housing portion and said second housing portion urge said elastomer member into a sealing arrangement with said at least glass slide member, said elastomer member having at least one channel, at least one inlet port and at least one outlet port and a material area;

wherein materials entering said housing though said at least one inlet port are transported through said at least one channel and out though said at least one outlet port.

9. The synthesis device as recited in claim 8 further comprising a material site affixed on said slide within said assay area.

10. The device as recited in claim 9 further comprising a window through said first housing portion adjacent to said material sight so that analysis of the material site may be performed therethrough.

11. The device as claimed in claim 8 wherein a plurality of inlet ports and a plurality of outlet ports are provided in said elastomer member.

12. The device as claimed in claim 8 wherein two glass slide members are provided, one positioned side of said elastomer member, and wherein said elastomer member has at least one channel on each side.

13. The device as claimed in claim 8 wherein said elastomer member provides a liquid tight seal on said glass slide member without the need for adhesives, gaskets or other sealing members between the glass slide member and the elastomer member.

14. The device as claimed in claim 8 wherein said elastomer member is made from a material selected from the group comprising polydimethylsiloxane (PDMS), liquid silicone rubber (LSR) or other elastomeric material having an inherent sealing affinity.

* * * * *

UNITED STATES PATENT AND TRADEMARK OFFICE

CERTIFICATE OF CORRECTION

PATENT NO. : 6,720,143 B2
APPLICATION NO. : 09/844980
DATED : April 13, 2004
INVENTOR(S) : Robert D. Juncosa et al.

It is certified that error appears in the above-identified patent and that said Letters Patent is hereby corrected as shown below:

Column 12,
Claim 8, line 30, should read as follows: -- one channel and out through said at least one outlet port. --

Column 12,
Claim 12, line 43, should read as follows: -- slide members are provided, one positioned on each side of said --

Signed and Sealed this

Twenty-second Day of August, 2006

JON W. DUDAS
*Director of the United States Patent and Trademark Office*